United States Patent
Gordon et al.

(10) Patent No.: US 6,709,128 B2
(45) Date of Patent: Mar. 23, 2004

(54) CURING SYSTEM

(75) Inventors: Samuel Y. Gordon, Newberg, OR (US); Edo Ziring, Mercer Island, WA (US); Larry DeSoto, Seattle, WA (US)

(73) Assignee: Ocumed, Inc., Vancouver, WA (US)

( * ) Notice: Subject to any disclaimer, the term of this patent is extended or adjusted under 35 U.S.C. 154(b) by 0 days.

(21) Appl. No.: 10/106,978

(22) Filed: Mar. 25, 2002

(65) Prior Publication Data

US 2002/0133970 A1 Sep. 26, 2002

Related U.S. Application Data

(60) Provisional application No. 60/289,733, filed on May 10, 2001, and provisional application No. 60/278,340, filed on Mar. 26, 2001.

(51) Int. Cl.⁷ .................................................. B25B 23/18
(52) U.S. Cl. ....................... 362/119; 362/109; 362/230; 362/294; 362/373; 250/504 H; 433/229
(58) Field of Search ............................... 362/109, 573, 362/294, 373, 190, 119, 230; 250/504 H; 433/229

(56) References Cited

U.S. PATENT DOCUMENTS

| | | | |
|---|---|---|---|
| 5,420,768 A | | 5/1995 | Kennedy |
| 5,457,611 A | * | 10/1995 | Verderber .................... 362/32 |
| 5,624,711 A | | 4/1997 | Sundberg et al. |
| 6,102,696 A | * | 8/2000 | Osterwalder et al. ......... 433/29 |
| 6,200,134 B1 | * | 3/2001 | Kovac et al. .................. 433/29 |
| 6,318,996 B1 | * | 11/2001 | Melikechi et al. ............. 433/29 |
| 6,331,111 B1 | * | 12/2001 | Cao ............................. 433/29 |
| 6,468,077 B1 | * | 10/2002 | Melikechi et al. ............. 433/29 |
| 6,517,218 B2 | * | 2/2003 | Hochstein .................... 362/294 |
| 6,523,979 B1 | * | 2/2003 | Kawata et al. .............. 362/294 |
| 6,611,110 B1 | * | 8/2003 | Fregoso ....................... 315/224 |

\* cited by examiner

*Primary Examiner*—Sandra O'Shea
*Assistant Examiner*—Jacob Y. Choi
(74) *Attorney, Agent, or Firm*—Kolisch Hartwell, P.C.

(57) ABSTRACT

The present invention provides a system for curing a curable material within a dimensionally restricted space, wherein the curable material is configured to be cured by exposure to electromagnetic radiation. The system includes a grip, an elongate portion extending from the grip, and a curing element coupled with the elongate portion at a location spaced from the grip. The curing element is configured to produce electromagnetic radiation of a wavelength suitable for curing the composite material.

27 Claims, 3 Drawing Sheets

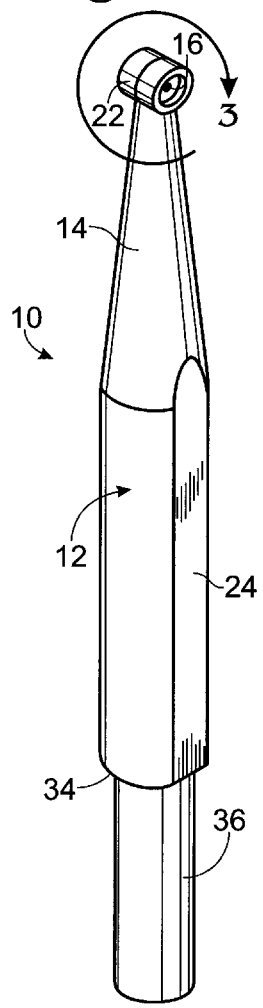
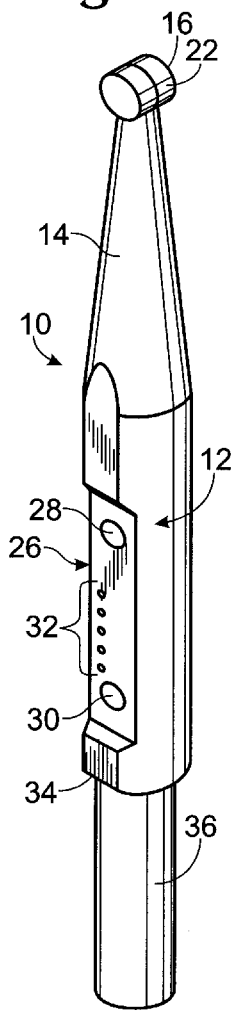
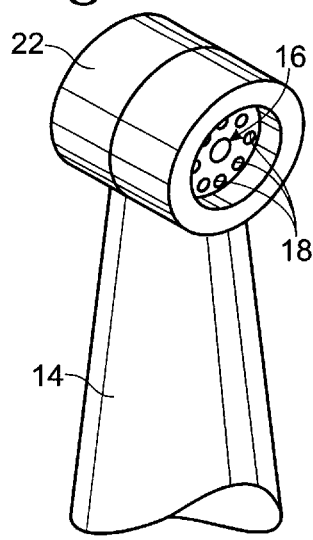
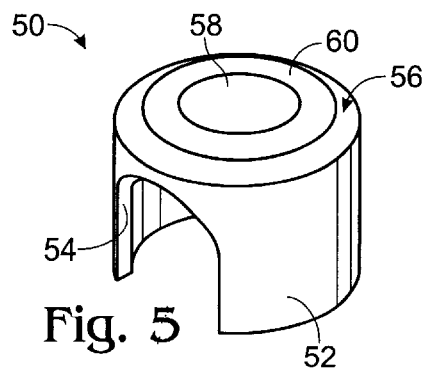
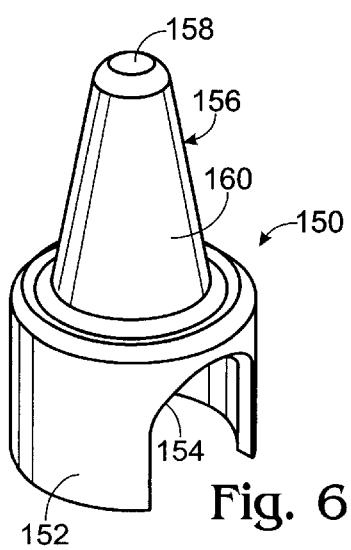

CURING SYSTEM

CROSS-REFERENCE TO RELATED APPLICATIONS

This application claims priority from U.S. Provisional Patent Application Serial No. 60/289,733, filed on May 10, 2001, and U.S. Provisional Patent Application Serial No. 60/278,340, filed on Mar. 26, 2001, the disclosures of which are hereby incorporated by reference.

TECHNICAL FIELD

The present invention relates to a lightweight curing system suitable for the curing of materials in a dimensionally restricted, heat-sensitive space.

BACKGROUND OF THE INVENTION

Curable materials that are activated or cured by exposure to electromagnetic radiation find applications in many different fields. For example, many electromagnetic radiation-activated (or "light-activated") materials are used in dentistry for such diverse purposes as tooth filling, prosthetic appliance fastening, light-activated tooth whitening and dental surface treatments. The use of such a material allows a user to apply the polymer carefully and without haste, as the material does not cure until the user applies electromagnetic radiation of a suitable wavelength to the material. Typically, electromagnetic radiation in the visible spectrum, and more typically in the blue spectrum, is used to cure the materials, although it will be appreciated that some materials may be cured by radiation outside of these spectra.

Various devices are available for curing light-activated materials. One commonly-used type of device is a hand-held device that includes a handle and a light-emitting tip configured to fit within a patient's mouth. The light source, typically a filtered halogen lamp, is generally contained within the handle. A light conduit, such as a bundle of optical fibers, a formed acrylic rod or a formed fused glass rod, is typically used to deliver the light to the tip.

Power is typically provided to the device by an external supply via an attached cord. However, various problems may be encountered in trying to place the power supply in a convenient and efficient location. For example, if the power supply is mounted to an office wall, the power cord may be stretched across the work area while the device is in use. The stretched cord may exert continuous tension against the user, and thus may cause user fatigue. Likewise, placing the power supply on the floor beneath the patient chair may require a user to bend over repeatedly to manipulate the power controls, possibly causing fatigue.

Known hand-held curing devices may have other problems. For example, the halogen lamps used in these devices may produce a great deal of heat, so a small fan configured to cool the lamp is often provided in the device handle. Due to the weight of the fan, lamp and light conduit, such a system may be bulky and heavy, and thus may cause user fatigue.

Yet another problem with known hand-held curing devices involves build-up of cured material on the device tip. When working in confined spaces such as a patient's mouth, the tip of the curing device extension may contact the curable material during the curing process. This may cause the curable material to adhere to and cure on the tip, and may necessitate a careful and time-consuming removal process. Furthermore, different tasks may require the use of light conduits of different diameters. This may require a user to purchase several light conduits of different sizes, and thus may increase the overall cost of the curing device.

SUMMARY OF THE INVENTION

The present invention provides a system for curing a curable material within a dimensionally restricted space, wherein the curable material is configured to be cured by exposure to electromagnetic radiation. The system includes a grip, an elongate portion extending from the grip, and a curing element coupled with the elongate portion at a location spaced from the grip. The curing element is configured to produce electromagnetic radiation of a wavelength suitable for curing the composite material.

BRIEF DESCRIPTION OF THE DRAWINGS

FIG. 1 is an isometric view of a first embodiment of a curing system according to the present invention.

FIG. 2 is an isometric view of the embodiment of FIG. 1, rotated approximately ninety degrees from the view of FIG. 1.

FIG. 3 is a magnified isometric view of the tip portion of the embodiment of FIG. 1.

FIG. 5 is an isometric view of a first exemplary tip cover for the embodiments of FIGS. 1 and 4.

FIG. 6 is an isometric view of a second exemplary tip cover for the embodiments of FIGS. 1 and 4.

DETAILED DESCRIPTION OF THE PREFERRED EMBODIMENTS

Figure 4:
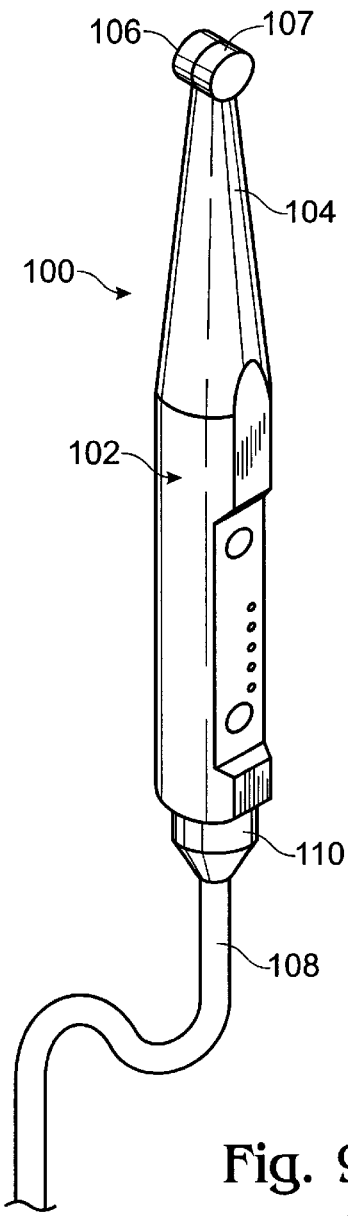
FIG. 4 is an isometric view of a second embodiment of a curing system according to the present invention.

A first embodiment of a curing system according to the present invention is shown generally at 10 in FIGS. 1–2. Curing system 10 includes a grip or handle portion 12, an elongate portion or extension 14 extending away from the grip, and a curing element 16 coupled with the elongate portion at a location spaced from the grip. Elongate portion 14 is configured to fit within a confined space, such as a dental patient's mouth, so that a curable material contained within the confined space may be illuminated with electromagnetic radiation from curing element 16.

Curing element 16 is configured to produce electromagnetic radiation of a wavelength suitable for curing a selected curable material. The placement of the electromagnetic-producing curing element 16 along the length of elongate portion 14, rather than within grip 12, may offer several advantages over conventional curing systems that place the electromagnetic radiation source within the device handle. For example, the placement of curing element 16 along the length of elongate portion 14 may allow the elimination of a conventional electromagnetic source within grip 12. This may allow the size of grip 12 to be decreased relative to conventional curing devices, and also may decrease the weight of the system. Furthermore, the placement of curing element 16 along the length of elongate portion 14 may eradicate the need for a fiber optic light conduit to be used to direct light from the curing element to the device tip. This may further decrease the weight of curing system 10 relative to conventional curing devices, and also may decrease the cost of the system.

Curing element 16 typically includes one or more small light-emitting devices 18 configured to output radiation of a wavelength suitable for curing a selected curable material. Because the rate at which the curable polymer cures is dependent upon the intensity of the incident light, it may be desirable to utilize a plurality or array of light emitting devices 18 in curing element 16 to attain an output of a higher radiant flux than possible with a single light emitting device. An exemplary array of light emitting devices 18 is shown in more detail in FIG. 3. Light emitting devices 18 typically take the form of light emitting diodes (LEDs) or diode lasers.

Curing element 16 may be configured to produce radiant energy of any suitable wavelength. For dental applications, many common curable polymers have an activation wavelength in the visible spectrum, typically within the blue range of the visible spectrum. For example, some common dental polymers are activated with light of a 472 nm wavelength. Thus, in one embodiment of the invention, the array of LEDs 18 may be configured to produce light of a wavelength of 472+/−10 nm.

Curing element 16 may be coupled with elongate portion 14 at any desired location along the elongate portion. In the embodiment of FIG. 1, curing element 16 is coupled to a distal end of elongate portion 14, but may also be located at a position spaced from the distal end, depending upon the intended application for the curing system. A housing 22 may be provided at distal end 20 of elongate portion 14 to hold curing element 16, and to direct light from curing element 16 in a desired direction.

Grip 12 and elongate portion 14 may have any suitable construction. Typically, grip 12 is made of either a metallic or molded plastic material. In the depicted embodiment, grip 12 has a cylindrical shape, but it will be appreciated that it may have any other suitable shape. Where a cylindrical grip 12 is used, one or more flats 24 may be formed in grip 12 to prevent system 10 from rolling when set on a smooth surface.

Grip 12 typically houses the electronics of curing system 10, and may include a control panel 26 to permit a user to operate these electronics. Control panel 26 may include any controls for any desired function. For example, control panel 26 may include a power off/on switch 28, a timer control switch 30, and a timer LED readout 32. Timer control switch 30 is typically configured to operate a timer circuit that controls the length of time that curing element 16 produces light. The length of time that curing element 16 is to produce light may be a factor of the type, amount and thickness of curable material applied. With knowledge of some or all of these factors, a user may use timer control switch 30 to select a predetermined amount of time for curing element 16 to illuminate the curable material for optimum curing. Also, the use of timer control switch 30 may help to prevent a user from leaving curing system 10 on after use.

Elongate portion 14 may be integral with grip 12, or may be formed as a separate part that is later attached to the grip. Elongate portion 14 typically has a reduced diameter relative to grip 12 to fit more easily within a restricted space, such as a patient's mouth. Elongate portion 14 may have either a solid or hollow construction, and may have any suitable diameter. Typically, the diameter of elongate portion 14 will be sufficient to allow electrical leads to be run through the elongate portion to curing element 16.

Elongate portion 14 may also be configured to accommodate passage of a coolant for cooling curing element 16. Depending upon the type and number of LEDs and/or diode lasers used for curing element 16, and the amount of power consumed by curing element 16, the curing element may have a relatively high thermal output. If curing element 16 becomes too hot, it may not function properly, or may become too hot to be used in a heat-sensitive area, such as in the mouth of a patient.

Any desired type of cooling system may be used. For example, a conventional fan-type cooling system, in which a fan is positioned within grip 12 and configured to circulate air by curing element 16, may be used. Alternatively, a compressed air cooling system, as depicted in FIGS. 1–2, may be used. To provide for cooling by compressed air, grip 12 may include a coupler, such as receptacle 34, configured to receive a compressed air source, such as a compressed air cylinder 36. Grip 12 and elongate portion 14 may include an air passage formed within their interiors to direct airflow from compressed air cylinder 36 across curing element 16. The air passage may also be configured to discharge used air through a vent (not shown). The release of air from compressed air cylinder 36 may be configured to occur automatically whenever power is supplied to curing element 16, or may be controlled via a control on control panel 26.

Any suitable power supply may be used to power curing system 10. For example, curing system 10 may utilize a battery (not shown) positioned within the interior of grip 12 to supply power to curing element 16. The use of a battery as a power supply for curing system 10 may be advantageous, as it may allow the curing system to be transferred between rooms as needed. Either a disposable or rechargeable battery may be used. Where a rechargeable battery is used, curing system 10 may include external electrical contacts (not shown) configured to connect to complementary contacts in an external charger (not shown) so that the battery does not need to be removed from grip 12 for recharging.

FIG. 4 shows, generally at 100, a second embodiment of a curing system according to the present invention. Curing system 100 is similar in many respects to curing system 10 of FIGS. 1–2. For example, curing system 100 includes a grip 102, an elongate portion 104 extending away from the grip, and a curing element 106 coupled with the elongate portion adjacent a distal end of the elongate portion. Curing element 106 may be contained within a housing 107 configured to protect curing element 106 and to direct light from curing element 106 in a desired direction.

However, unlike curing system 10, curing system 100 is configured to accept the attachment of an external power and air cord 108. Power and air cord 108 is configured to deliver power to curing element 106, and also to deliver a flow of air to cool the curing element. Power and air cord 108 is typically fastened to grip 102 with a suitable connector 110 so that curing system 100 may be quickly and easily disconnected from power and air cord 108 for storage, or so that another device may be connected to the power and air cord. In addition to receiving both power and air via an external cord, it will be appreciated that curing system 100 may also utilize an external cord to receive either power or air alone.

A curing system according to the present invention is typically held spaced from the surface of a curable material when being used to cure the material. However, as mentioned above, the curing element may accidentally come into contact with the curable material during a curing process.

Ordinarily, this may require an expensive and time-consuming clean-up procedure to remove the material from the system. However, in some embodiments of the present invention, the curing system may include a removable tip that protects the curing element from being contaminated with curable material.

FIGS. 5 and 6 show two exemplary embodiments of removable tips. While the removable tips of the depicted embodiments are described herein in the context of curing system 10, it will be appreciated that the features and concepts regarding the removable tips may be adapted for use any curing system according to the present invention.

Referring first to FIG. 5, removable tip 50 includes a generally cylindrical body 52 configured to fit around and over curing element housing 22. Cylindrical body 52 is typically at least somewhat rigid, and may be configured to snap over the back of housing 22 to secure removable tip 50 to device 10. Cylindrical body 52 typically includes a recess 54 configured to accommodate elongate portion 14 when removable tip 50 is inserted over housing 22.

Removable tip 50 also includes a top portion 56. Top portion 56 typically has a transparent or translucent portion 58 configured to be positioned over curing element 16 when removable tip 50 is mounted to curing system 10. Translucent portion 58 may be surrounded by an outer, opaque portion 60 if it is desired to reduce the diameter of the curing light spot.

The use of a curing system with removable tip 50 may offer several advantages over the use of a curing system without the removable tip. For example, the size of the curing light spot may be varied by the selection of removable tips with different-sized translucent portions. Also, if removable tip 50 is contaminated with curable material during a curing process, the tip may simply be discarded and replaced. Furthermore, packaging disposable tip 50 in a sterilized package may allow curing system 10 to be used without sterilization between patients, simply by using a new disposable tip 50 for each patient. Removable tip 50 is typically constructed of plastic, but also may be constructed of any other suitable material.

FIG. 6 shows, generally at 150, a second exemplary removable tip. Removable tip 150 includes a generally cylindrical body 152 configured to fit over curing element housing 22, and may include a recess 154 configured to accommodate elongate portion 14 while removable tip 150 is in place over housing 22.

Removable tip 150 also includes an extension 156 that extends away from cylindrical body 152. Extension 156 typically includes opaque sides 160, and is capped with a transparent or translucent portion 158. Thus, light is emitted from removable tip 150 only from translucent portion 158. The use of extension 156 may allow the generation of a very small light spot, and also may facilitate positioning of the light spot.

Figure 7:
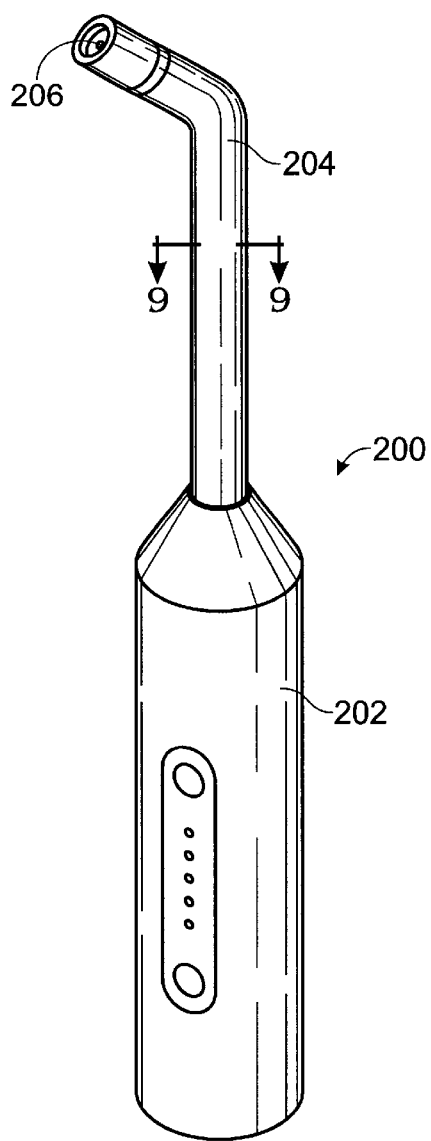
FIG. 7 is an isometric view of a third embodiment of a curing system according to the present invention.
Figure 9:
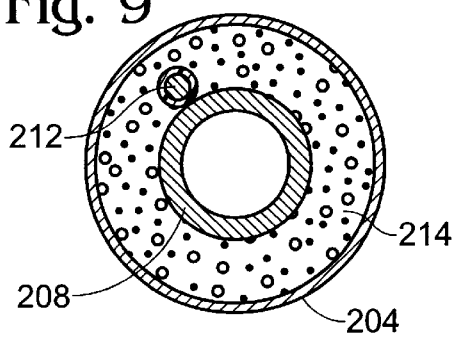
FIG. 9 is a sectional view of the extension of the embodiment of FIG. 7, taken along line 9—9 of FIG. 7.

FIGS. 7–10 depict, generally at 200, a third embodiment of a curing system according to the present invention. Referring first to FIG. 7, curing system 200 includes a grip 202, an elongate portion 204 extending away from the grip, and a curing element 206 coupled with the elongate portion at a location spaced from the grip. Curing element 206 is configured to produce electromagnetic radiation of a desired wavelength, and typically includes one or more LEDs or diode lasers as light emitting elements.

Figure 8:
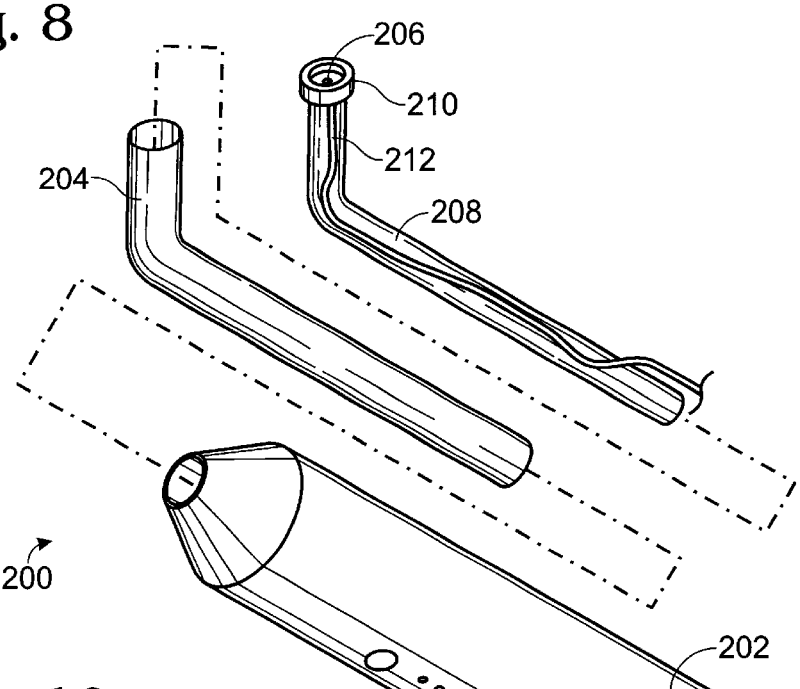
FIG. 8 is an exploded isometric view of the embodiment of FIG. 7.

Curing system 200 also typically include a thermally conductive heat transfer element, shown at 208 in FIG. 8, configured to conduct heat away from curing element 206 for more rapid dissipation. Heat transfer element 208 is configured to conduct heat away from curing element 206 rapidly enough to keep the curing element cool enough for reliable operation, and cool enough for use in heat-sensitive areas.

To facilitate the transfer of heat from curing element 206 to heat transfer element 208, the curing element may be mounted to a thermally conductive mount 210. Thermally conductive mount 210 is typically formed of a highly thermally conductive metal. Likewise, curing element 206 is typically bonded to mount 210 with a high thermal conductivity epoxy, although it will be appreciated that other thermally conductive materials may also be used for the mount and bonding agent. Furthermore, mount 210 may include an aperture or recess to accommodate electrical leads 212 for supplying power to curing element 206.

Heat transfer element 208 is joined to mount 210 to conduct heat away from the mount, and thus away from curing element 206. Heat transfer element 208 is typically joined to mount 210 in a manner that ensures the rapid transfer of heat from the mount to the heat transfer element. Typically, heat transfer element 208 is joined to mount 210 with a thermally conductive epoxy or a low temperature metal braze, although other methods may be used if desired.

Curing system 200 also typically includes a heat sink in thermal communication with heat transfer element 208. The heat sink is configured to rapidly dissipate heat that is conducted away from curing element 206 by heat transfer element 208. One example of a suitable heat sink is shown at 214 in FIG. 9 as a thermally conductive molded material that surrounds heat transfer element 208 within the interior of elongate portion 204. Heat sink 214 is typically formed from a thermally conductive epoxy, and more typically from a thermally conductive epoxy with a high specific gravity. Heat sink 214 may be formed by first inserting heat transfer element 208 into elongate portion 204, and then filling the remaining volume of the interior of the elongate portion with the material from which the heat sink is formed. This may create a large surface contact area between heat transfer element 208 and heat sink 214, and thus may help dissipate heat rapidly to keep curing element 206 at a uniform temperature. It will be appreciated that the entire elongate portion 204/curing element 206/heat transfer element 208/mount 210/heat sink 214 assembly may be made rotatable (using an axial or circumferential electrical contact system) and replaceable to offer different curing patterns and sizes.

Figure 10:
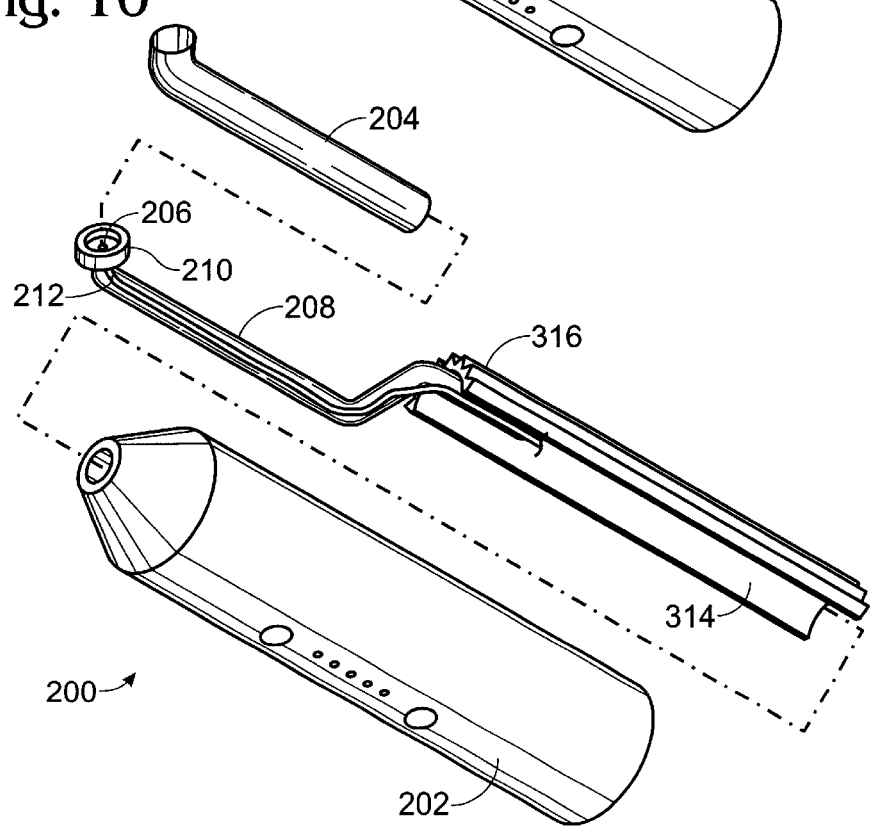
FIG. 10 is an exploded isometric view of the embodiment of FIG. 7, showing an alternate heat sink configuration.

FIG. 10 depicts, generally at 314, a second, alternative embodiment of a heat sink suitable for use with curing system 200. Rather than utilizing a thermally conductive epoxy that surrounds heat transfer element 208, heat sink 314 includes a metal (or other thermally conductive material) body joined to the opposite end of heat transfer element 208 as mount 210. Heat transferred to heat sink 314 from thermal conductor 208 is rapidly dissipated by heat sink 314, due to the relatively large mass and surface area of the heat sink.

Heat sink 314 is typically formed from a highly thermally conductive metal, such as aluminum or copper, and is typically joined to mount 210 with a thermally conductive epoxy or a condenser joint. Heat sink 314 may be fabricated via any desired process, for example an extrusion process. Heat sink 314 may have a curved shape contoured to fit the inside of grip 202, and also may have a plurality of raised fins 316 to increase the surface area of heat sink 314. While heat sinks 214 and 314 are shown used exclusively of each other in the depicted embodiments, it will be appreciated that heat sinks 214 and 314 may also be used together in a single curing system. Furthermore, a compressed air or fluid cooling system may be used either in place of, or in conjunction with, either of heat sinks 214 and 220 to dissipate heat transferred from curing element 206.

A curing system according to the present invention may also include an active thermal monitoring system. Typically, a thermal monitoring system is configured to measure changes in the temperature of each light emitting device within the curing element by detecting changes the voltage drop across the junction of the light emitting device. The actual temperature of the light emitting device may be determined by comparison of the measured change in voltage to a predetermined voltage measured at a known temperature. For example, where LEDs are used as the curing element, the voltage drop across the junction of each LED decreases by approximately 2 millivolts for each 1 degree Celsius rise in temperature of the junction. The measured voltage may be subtracted from the predetermined voltage to determine the change in voltage, and then the temperature may be calculated from the voltage change.

The active thermal monitoring system may also be configured to shut off the curing element when the actual temperature of the junction goes above a predetermined threshold temperature, and to turn the curing element back on once the temperature drops below the threshold value. This may help to prevent thermal damage from occurring to the curing element, and thus may help increase the lifetime of the curing system.

A curing system according to the present invention may offer several advantages over conventional curing systems. For example, a curing system according to the present invention is typically lighter, less bulky, and less complex than conventional devices. Also, a curing system according to the present invention may be less expensive to manufacture than a conventional curing system due to the elimination of the costly fiber optics used in conventional devices. Furthermore, the use of a compressed air cooling system may make a curing system according to the present invention lighter, less bulky, and less noisy than conventional devices. Additionally, the use of a disposable tip may allow the size of the curing spot to be quickly and easily varied, may help to prevent the spread of infection, and may serve as precision spacer between the curing element and the prepared surface that is to be cured. Finally, a curing system according to the present invention may have a similar look and feel to other dental tools. This may allow a user to learn to operate the device quickly and easily, and also may allow a curing system according to the present invention to be used in conjunction with standard dental tool holders, thus allowing the device to be positioned at a standard and predictable location within a dental office.

The disclosure set forth above encompasses multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious and directed to one of the inventions. These claims may refer to "an" element or "a first" element or the equivalent thereof; such claims should be understood to include incorporation of one or more such elements, neither requiring nor excluding two or more such elements. Inventions embodied in other combinations and subcombinations of features, functions, elements, and/or properties may be claimed through amendment of the present claims or through presentation of new claims in this or a related application. Such claims, whether directed to a different invention or to the same invention, and whether broader, narrower, equal, or different in scope to the original claims, also are regarded as included within the subject matter of the inventions of the present disclosure.

We claim:

1. A system for curing a curable material in a dimensionally restricted space, wherein the curable material is configured to be cured by exposure to electromagnetic radiation, the system comprising:
   a grip;
   an elongate portion extending from the grip, wherein the elongate portion is configured to be inserted into the dimensionally restricted space;
   a curing element coupled with the elongate portion at a location spaced from the grip, wherein the curing element is configured to produce electromagnetic radiation of a wavelength suitable for curing the composite material; and
   a heat transfer element positioned within the elongate portion, wherein the heat transfer element is configured to transfer heat from the curing element to a location outside of the dimensionally restricted space for dissipation.

2. The system of claim 1, the elongate portion including a distal end, wherein the curing element is coupled with the elongate portion adjacent the distal end.

3. The system of claim 1, wherein the curing element includes an LED.

4. The system of claim 3, wherein the LED is coupled to a thermally conductive mount, and wherein the thermally conductive mount is connected to the heat transfer element.

5. The system of claim 1, further comprising a heat sink disposed within the elongate portion, wherein the heat sink is in thermal communication with the heat transfer element and is configured to dissipate heat transferred by the heat transfer element from the curing element.

6. The system of claim 5, wherein the heat sink includes a thermally conductive material at least partially surrounding the heat transfer element in the hollow interior.

7. The system of claim 6, wherein the thermally conductive material includes a thermally conductive epoxy.

8. The system of claim 6, wherein the grip includes an interior with a heat sink positioned at least partially therein, and wherein the heat transfer element is configured to conduct heat from the curing element, through the elongate portion and to the heat sink for dissipation.

9. The system of claim 8, wherein the heat sink includes at least one heat dissipating fin.

10. The system of claim 1, wherein the grip is configured to hold a battery for powering the system.

11. The system of claim 1, further comprising a compressed gas connector configured to couple the system to a compressed gas source for cooling the system.

12. The system of claim 1, wherein the system is configured to cure a dental composite, and wherein the elongate portion is configured to fit within the mouth of a patient.

13. The system of claim 1, further comprising a selectively removable tip piece coupled to the extension.

14. The system of claim 13, wherein the tip piece includes a translucent portion surrounded by an opaque portion.

15. The system of claim 14, wherein the tip piece includes an extension configured to increase a distance between the curing element and the translucent portion to reduce the size of a light spot produced by the system.

16. The system of claim 1, wherein the system is configured to detect a temperature of the curing element by monitoring a voltage across the curing element.

17. A system for curing a curable material within a space of restricted dimension, wherein the curable material is configured to be cured by exposure to electromagnetic radiation, the system comprising:

a grip;

an elongate portion extending away from the grip, the elongate portion having a distal end and being configured to fit within the space of restricted dimension;

a curing element coupled with the elongate portion adjacent the distal end, wherein the curing element is configured to produce electromagnetic radiation of a wavelength suitable for curing the composite material; and a heat transfer element disposed within the elongate portion, wherein the heat transfer element is configured to transfer heat from the curing element to a heat sink configured to be located outside of the space of restricted dimension for dissipation.

18. The system of claim 17, wherein the heat sink is disposed in a location remote from the curing element and is thermally connected to the curing element by the heat transfer element.

19. The system of claim 18, wherein the elongate portion includes an interior, and wherein the heat sink is disposed within the interior of the elongate portion.

20. The system of claim 18, wherein the grip includes an interior, and wherein the heat sink is disposed within the interior of the grip.

21. The system of claim 17, further comprising a thermally conductive mount to which the curing element is mounted, wherein the heat transfer element is coupled to the thermally conductive mount.

22. The system of claim 17, wherein the system is a dental system, and wherein the elongate portion is configured to fit within a mouth.

23. A system for curing a curable material in a heat-sensitive, dimensionally restricted location, the curable material being configured to be cured by exposure to electromagnetic radiation, the curing system comprising:

a grip;

an elongate portion extending away from the grip, the elongate portion having an interior and including a heat transfer element disposed within the interior;

a curing element coupled with the elongate portion and in thermal communication with the heat transfer element, wherein the curing element is configured to produce electromagnetic radiation suitable for curing the composite material; and a heat sink positioned remotely from the curing element and connected to the heat transfer element, wherein the heat transfer element is configured to conduct heat away from the curing element to the heat sink for dissipation.

24. The system of claim 23, wherein the heat sink is disposed within the grip.

25. The system of claim 23, wherein the heat sink is disposed within the elongate portion at a location configured to be outside of the dimensionally restricted space during a curing process.

26. The system of claim 1, wherein the heat sink is formed from a thermally conductive material that essentially fills a space in the elongate portion between the heat transfer element and an outer wall of the elongate portion.

27. The system of claim 26, wherein the heat sink is formed from a thermally conductive epoxy.

* * * * *